United States Patent [19]

Szentmiklósi et al.

[11] Patent Number: 5,064,815
[45] Date of Patent: Nov. 12, 1991

[54] PRIMYCIN-CONTAINING COLLOIDAL BASIC GEL

[75] Inventors: Peter Szentmiklósi; Tamás Szüts; József Nemes; József Lengyel; Jenö Marton; Peter Sárközi; Erzsébet Babos née Vajas; Enikö Schreiner née Kovats, all of Budapest, Hungary

[73] Assignee: Chinoin Gyogyszer es Vegyeszeti Termekek Gyara RT., Budapest, Hungary

[21] Appl. No.: 500,236

[22] Filed: Mar. 26, 1990

Related U.S. Application Data

[63] Continuation of Ser. No. 277,424, Nov. 25, 1988, abandoned, which is a continuation-in-part of Ser. No. 935,860, Nov. 26, 1986, abandoned.

[30] Foreign Application Priority Data

Nov. 27, 1985 [HU] Hungary .............................. 4526/85
Nov. 14, 1986 [HU] Hungary .............................. 4689/86

[51] Int. Cl.⁵ ...................... A61K 31/70; C07H 17/08
[52] U.S. Cl. ........................................ 514/31; 536/6.5
[58] Field of Search ........................... 514/31; 536/6.5

[56] References Cited

U.S. PATENT DOCUMENTS

| | | | |
|---|---|---|---|
| 4,132,781 | 1/1979 | Stoughton | 514/29 |
| 4,268,498 | 9/1981 | Gedeon et al. | 424/59 |
| 4,537,776 | 8/1985 | Cooper | 514/424 |
| 4,557,934 | 12/1985 | Cooper | 514/231 |

FOREIGN PATENT DOCUMENTS 0756856  3/1971  Hungary .............................. 514/31

OTHER PUBLICATIONS

Merck Index, 10th Ed., Compound 7652.
The Condensed Chemical Dictionary, 10th Ed., Hawley, pp. 97 and 1127 (1981).

*Primary Examiner*—Elli Peselev
*Attorney, Agent, or Firm*—Herbert Dubno; Jonathan Myers

[57] ABSTRACT

This invention relates to a primycin-containing colloidal basic gel comprising 5-30% of primycin and 95-70% of N-methyl-pyrrolidone-2. The invention also relates to antibacterial compositions particularly for the treatment of acne vulgaris comprising as active ingredient 0.1-100% of a primycin-containing colloidal basic gel, if desired together with further antimicrobial active ingredients, in admixture with 99.9-0% of usual inert pharmaceutical filling, diluting and other formulating additives. The invention also relates to combination composition comprising as active ingredient 1-60% of a primycin-containing colloidal basic gel and 0.1-40% of further pharmaceutical active ingredient(s), e.g. one or more antibiotic(s), chemotherapeutical agent(s), fungistatic or fungicidal agent(s), steroidal or non-steroidal antiinflammatory agent (s), epithelogenic agent(s), local anaesthetic(s), and/or vitamin(s).

11 Claims, No Drawings

PRIMYCIN-CONTAINING COLLOIDAL BASIC GEL

This is a continuation of co-pending application Ser. No. 07/277,424 filed on 25 Nov. 1988 now abandoned which is a continuation-in-part of Ser. No. 06/935,860 filed 26 Nov. 1986 now abandoned.

This invention relates to a primycin-containing colloidal basic gel, a process for the preparation thereof, pharmaceutical and pharmaco-cosmetical compositions comprising the same and a process for the preparation of the said compositions.

Primycin is a macrolid antibiotic characterized in the prior art [J. Chem. Soc., Perkin I. page 816 (1974)] by a single Formula, namely [5-(18-($\alpha$-D-arabinofuranosyloxy)-2-butyl-3,7,11,15,19,21,23,25,27-nonahydroxy-4,16,32,34-tetramethyl-1-oxo-oxacyclohexatriaconta-16,32-dien-35-yl)-4-hydroxyhexyl]-guanidinium-sulfate.

Although in the prior art the said antibiotic is characterized by a single Formula it is known that it is an antibiotic complex consisting of various components (Hungarian patent application ser. No. 2125/84 and 2869/84). Primycin is a natural antibiotic obtained from the culture of the fungal strain Thermopolyspora galeriensis and the production of the said antibiotic by fermentation is disclosed in Hungarian patent No. 153,593. Primycin is broad-spectrum antibiotic be particularly effective against gram-positive bacteria but active against polyresistant human pathogenic strains as well. No resistance has developed against Primycin so far. Primycin exhibits a synergistic effect when administered with other antibiotics (Hungarian patent No. 158,241). Primycin can be preferably used in dermatology, surgery ophthalmology, urology, gynaecology, pneumonotherapy and in the treatment of household and burn injuries. Primycin is particularly useful in dermatology in the treatment of acne vulgaris.

The extremely low solubility of primycin makes the therapeutical use thereof difficult because it is very difficult to prepare a composition form which makes the active ingredient readily available. An attempt has been made to overcome this drawback by forming a stable heterocolloid having a primycin content of 0.2% in an aqueous alcoholic medium (Hungarian patent No. 173,708).

The primycin-containing heterocolloid thus obtained has, however, two fundamental drawbacks; on the one hand the evaporation of the solvent makes the active ingredient biologically unavailable while on the other hand the highest achievable concentration amounts only to 0.2%. This limits the applicability of the composition because the active ingredient content of similar antibiotic compositions used for the treatment of Acne vulgaris reaches the value of 1-2%.

It is the object of the present invention to provide a suitable form of primycin which enables the preparation of pharmaceutical and/or pharmaco-cosmetical compositions meeting the above requirements.

The present invention is based on a surprising recognition, which enables the preparation of any composition form comprising 0-30% of primycin. Thus it has been found that on dissolving primycin in N-methyl-pyrrolidone-2, referred to furtheron as NMP, a basic gel of a stable structure is obtained which enables the preparation of various pharmaceutical compositions having a higher primycin content than the hitherto known compositions.

It has been found that on dissolving 5-30 g of primycin in 100 ml of N-methyl-pyrrolidone-2 at 100° C. and thereafter cooling the solution a stable gel is obtained which may be either directly applied or can be used as a basic starting material for the preparation of any usual compositions (e.g. gel, ointment, spray, solution, etc.).

According to an aspect of the present invention there is provided a primycin-containing colloidal basic gel comprising 5-30% of primycin and 95-70% of N-methyl-pyrrolidone-2.

The said basic gel according to the present invention comprises preferably 10-20% of primycin and 90-80% of N-methyl-pyrrolidone-2.

According to a further aspect of the present invention there is provided a process for the preparation of a primycin-containing colloidal basic gel which comprises dissolving 5-30% of primycin in 95-70% of N-methyl-pyrrolidone-2 at a temperature of 50°-150° C., if desired under stirring, and thereafter cooling the solution to room temperature.

One may proceed preferably by dissolving 10-20% of primycin in 90-80% of N-methyl-pyrrolidone-2. The process may be preferably accomplished at a temperature between 70° and 100° C.

According to a further aspect of the present invention there are provided antibacterial compositions particularly for the treatment of acne vulgaris comprising as active ingredient 0.1-100% of a primycin-containing colloidal basic gel, if desired together with further antimicrobial active ingredients, in admixture with 99.9-0% of the usual inert pharmaceutical filling, diluting and other formulating additives.

According to a still further aspect of the present invention there is provided a combination composition according to the fact mentioned above, comprising as active ingredient 1-60% of a primycin-containing colloidal basic gel and 0.1-40% of further pharmaceutical active ingredient(s), e.g. one or more antibiotic(s), chemotherapeutical agent(s), fungistatic or fungicidal agent(s), steroidal or non-steroidal antiinflammatory agent(s), epitheliogenic agent(s), or (a) anaesthetic(s), and/or vitamin(s).

The said antibacterial pharmaceutical and/or pharmaco-cosmetical compositions may be prepared by finishing a colloidal basic gel comprising primycin and further antibacterial active ingredient(s), preferably an antibiotic, with the aid of carriers, fillers and auxiliary agents generally used for the manufacture of pharmaceutical and/or pharmaco-cosmetical compositions in the form of pharmaceutical and/or pharmaco-cosmetical compositions.

The compositions may be finished in any suitable conventional form, preferably as gel, ointment, solution, spray or any other form suitable for local use.

One may proceed preferably by finishing the composition in the form of a gel, ointment, paste, solution, spray, painting solution, dusting powder or any composition suitable for local application or in the form of a bandage or plaster by applying onto a sterile mull sheet in a known manner.

N-methyl-pyrrolidone-2 is a solvent frequently used in cosmetical compositions. In cosmetics the advantage is unlimited miscibility with water, organic solvents and fats. This property makes N-methyl-pyrrolidone-2 particularly suitable for the preparation of primycin-containing pharmaceutical compositions because if the above gel is finished by admixing with any solvent or additive the original gel structure is restored during use under the evaporation or absorption of the solvent. This enhances the penetration of primycin between the aqueous and lipid biological phases in a valuable and efficient manner.

We have studies spontaneous gel-formation with various solvents on the one hand and various pharmaceutical active ingredients on the other. The following solvents are used: methanol, ethanol, isopropanol, n-butanol, isobutanol, dichloromethane, chloroform, carbon tetrachloride, ethyl acetate, acetonitrile, n-hexane, petrol, benzene, toluene, petrolether, ether, dimethyl formamide, dimethyl sulfoxide, isopropyl myristate. None of the above solvents forms a stable gel with primycin.

Although other solvents (e.g. ethanol amine, diethanol amine, triethanol amine, dimethyl formamide, dimethyl sulfoxide) form a gel with primycin, in the tested concentration interval (5–30%) pure gel is formed neither in the cold nor in the warm and consequently the said solvents are unsuitable for the preparation of pharmaceutical formulations.

Furtheron gel-formation has been studied between N-methyl-pyrrolidone and further pharmaceutical active ingredients. The following active ingredients are used: gentamycin, doxycyclin, oxolinic acid, nalidixic acid, drotaverin, theophyllin, acetyl salicylic acid, papaverin, indomethacin. None of the above active ingredients form a stable transparent gel with N-methyl-pyrrolidone.

Thus only the interaction between primycin and N-methyl-pyrrolidone gives rise to spontaneous gel-formation resulting in the formation of a stable transparent gel.

We have studied furtheron the possibility of the preparation of mixed gels comprising two active ingredients, including antibiotics other then primycin (e.g. gentamicin, doxycyclin, oxytetracyclin, chloramphenicol etc.). It has been found that on adding a solution of primycin in N-methyl-pyrrolidone-2 a further antibiotic in solid form, no gel-formation takes place. On the other hand if doxycyclin and gentamycin are dissolved in water and the solution thus obtained is added to the solution of primycin in N-methil-pyrrolidone-2 gel formation begins and *hydrogels* comprising two active ingredients (namely primycin+doxycyclin and primycin+gentamycin, respectively) are obtained.

The said specific interaction between primycin and N-methyl-pyrrolidone-2 can be attributed in the one hand to the temperature-dependance of the solubility (between 0° and 100° C. more than two orders of magnitude) and the multi-component composition of primycin on the other.

The stability and also the change of the chemical and microbiological activity of the basic primycin basic gel according to the present invention is tested. A basic gel comprising 20% of primycin is allowed to stand at 100° C. for 5 hours and stored at room temperature for a month and at +5° C. for a month. During storage neither the structure nor the chemical composition and the microbiological activity of the gel changes, thus gel-formation does not alter the properties of primycin being important from the point of view of pharmaceutical utilization.

The stable gel thus formed may be used as basic material for the preparation of primycin-containing pharmaceutical and veterinary compositions. The said primycin-containing compositions prepared from the stable gel may be either used in monotherapy or can be combined with other active ingredients (e.g. antibiotics, chemotherapeutical agents, steroidal or non-steroidal antiinflammatory agents, epitheliogenic agents, vitamins, local anaesthetics etc.).

Further details of the present invention are to be found in the following Examples, without limiting the scope of protection to the said Examples.

EXAMPLE 1

Basic Gel having a Primycin Content of 20%

20.0 g of Primycin are dissolved in 80.0% of N-methyl-pyrrolidone-2 on a water-bath having a temperature of 100° C. Gel-formation begins already during the dissolving and is completed after cooling. The basic gel thus obtained is used for the preparation of the pharmaceutical compositions.

EXAMPLE 2

Aqueous Gel Comprising 0.5% Primycin 9.75 g AUICEL microcrystalline Cellulose (FMC Corporation, Philadelphia, U.S.A.) are homogenized in small portions with 87.75 g of distilled water at room temperature under constant stirring. The gel thus formed is further homogenized with 2.5 g of a 20% basic gel.

EXAMPLE 3

Aqueous Gel Comprising 1.0% of Primycin 9.50 g of Avicel RC 581 (FMC Company, Philadelphia, U.S.A.) are homogenized in small portions with 85.5 g of distilled water at room temperature under constant stirring. The gel thus formed is further homogenized with 5.0 g of a 20% basic gel.

EXAMPLE 4

Alcoholic Gel Comprising 1.0% of Primycin 5.0 g of a 20% basic gel are dissolved in 10.0 g of 96% alcohol under slight warming. In an other flask 8.5 g of Avicell RC 581 (FMC Company, Philadelphia, U.S.A.) are homogenized in small portions with 76.5 g of distilled water at room temperature under constant stirring. After further homogenization the gel thus formed is admixed with the primycin-containing alcoholic solution.

EXAMPLE 5

Aqueous Gel Comprising 2.0% of Primycin 9.00 g of Ultraamylopectin (SERVA Feinbiochemie, Heidelberg, GFR) are homogenized in small portions with 81.0 g of distilled water at room temperature under constant stirring. The gel thus obtained is homogenized with 10.0 g of a 20% basic gel.

EXAMPLE 6

Aqueous Gel Comprising 10% of Primycin 5.00 g of Avicel RC 581 (FMC Corporation, Philadelphia, U.S.A.) are homogenized in small portions with 45.0 g of distilled water at room temperature under constant stirring. The gel thus formed is homogenized with 50 g of 20% basic gel.

EXAMPLE 7

Alcoholic Gel Comprising 10% of Primycin 50.0 g of a 20% basic gel are homogenized with 50.0 g of 96% alcohol.

EXAMPLE 8

Carbowax Ointment Comprising 0.5% of Primycin 44.50 g of Carbowax 400 (Polyoxaethenum 400, USNF), 15.10 g of Carbowax 1540 (Polyoxaethenum 1540, USM), 21.45 g of Carbowax 4000 (Polyoxaethenum 4000, USNF), 9.75 g of glycerin 1, 1.85 g of alcohol cetyl stearilicus and 4.85 g of sorbitol are melted on a water bath. The melt ointment basic material thus obtained is homogenized in small portions with 2.5 g of a 20% basic gel under stirring.

EXAMPLE 9

Alcoholic Ointment Comprising 0.5% of Primycin 2.5 g of a 20% basic gel are dissolved in 200 g of 96% alcohol under slight warming.

35.25 g of Carboway 400, 12.00 g of Carboway 1540, 17.05 g of Carbowax 4000, 7.75 g of glycerin, 1.55 g of alcohol cetyl stearilicus and 3.80 g of sorbitol are melted on a water bath.

The melt ointment basic material thus obtained is homogenized in small portions with the alcoholic solution of the active ingredient under constant stirring. The ointment is filled up with Carbowax 400 to 100.00 g and cooled under stirring.

EXAMPLE 10

Carbowax Ointment Comprising 2% of Primycin 38.60 g of Carbowax 400, 13.20 g of Carbowax 1540, 18.70 g of Carbowax 4000, 8.5 g of glycerin, 1.80 g of alcohol cetyl stearilicus, 4.20 g of sorbitol and 5.0 g of lactyl are melt on a water bath.

The melt ointment basic material thus obtained is homogenized in small portions with 10.00 g of 20% basic gel under constant stirring.

EXAMPLE 11

Alcoholic Ointment Comprising 10.0% of Primycin 50.0 g of a 20% basic gel are homogenized with 20.0 g of 96% alcohol.

13.65 g of Carbowax 400, 4.65 g of Carbowax 1540, 6.60 g of Carbowax 4000, 3.00 g of glycerin, 0.6 g of alcohol cetyl stearilicus and 1.50 g of sorbitol are melted on a water bath.

The melt ointment basic material thus obtained is homogenized with the gel comprising the active ingredient in small portions under constant stirring. The ointment is filled up with Carbowax 400 to 100.0 g and cooled under stirring.

EXAMPLE 12

Comprising 2% of Primycin 10.0 g of 20% basic gel are dissolved in a mixture of 40.0 g of N-methyl-pyrrolidone-2 and 50.0 g of alcohol.

EXAMPLE 13

Ointment Comprising Primycin and other Active Ingredients a) Ointment Comprising Primycin + Hydrocortisone + Nystatin

| Component | Amount (g) |
|---|---|
| Primycin | 20.00 |
| Hydrocortisone | 20.00 |
| Nystatin | 20.00 |
| N-Methyl-pyrrolidone-2 (NMP) | 40.00 |

From 20 g of Primycin and 40.0 g of N-methyl-pyrrolidone-2 a gel is prepared at 70° C., whereupon nystatin and hydrocortisone are added at room temperature under constant stirring. A very viscous solution is obtained which becomes gelous on standing for 24 hours.

b) Ointment Comprising 1% of Primycin + 1% of Hydrocortisone + 1% of Nystatin (300.000 IU)

| Component | Amount (g) |
|---|---|
| Primycin + hydrocortisone + nystatin NMP gel | 5.0 |
| Alcohol cetyl stearilicus | 10.0 |
| Emulsifier E 2155 (T. Goldschmidt, Essen, GFR) | 5.0 |
| Distilled water ad | 100.0 |

The alcohol cetyl stearilicus and emulsifier E 2155 (stearyl alcohol polyglycol ether, manufacturer: T. Goldschmidt, Essen, GFR) are melted on a water-bath under constant stirring at 60°–70° C. About 80% of the distilled water having the same temperature is added under constant stirring in a thin stream. The gel is further homogenized with the previously prepared primycin + hydrocortisone + nystatin NMP gel and finally filled up with distilled water.

The ointment thus obtained can be used for the local treatment of bacterial and fungal infections.

EXAMPLE 14

Composition for the Treatment of Human Mastitis

| Component | Amount, to 100.00 g |
|---|---|
| Primycin-NMP basic gel comprising 20% of primycin | 10.0 |
| Glycerol | 10.0 |
| Tannic acid | 5.0 |
| Basic ointment | 75.0 |
| | 100.0 |

Basic Ointment

| Component | Amount (g) |
|---|---|
| Sodium lauryl sulfate | 40.0 5.i |
| Distilled water | 1.5 |
| Alcohol cetyl stearylicus | 36.0 |
| Paraffinum liquidum | 20.0 |
| Vaselin album | 40.0 |

The sodium lauryl sulfate and the water heated to boiling are admixed with cetyl stearyl alcohol melt and heated to about 90° C. on a water-bath. The liquid is vigorously stirred and heated to about 110°–120° C., until strong foaming ceases, whereupon the somewhat cooled liquid is admixed with the melt of liquid paraffin and vaseline. The melt is cooled under stirring.

4.0 g of the above melt are warmed on a water-bath to about 65°–70° C., whereupon it is introduced into a pre-heated mortar and a mixture of 1.0 g of solutio conservans and 50.0 g of distilled water heated to about 65°–70° C. is emulsified in the mixture under constant stirring. The ointment is stirred first vigorously and later carefully until it is cooled and a gel is formed whereupon it is filled up to 100.0 g with distilled water.

Ointment Comprising a Primycin Basic Gel

Tannic acid of the given amount is suspended in glycerol whereupon it is homogenized with a primycin-NMP basic gel and the basic ointment having room temperature is added in portions. The mixture is completely homogenized.

EXAMPLE 15

"For the Day Use" Cream

| Component | Amount (for 100.00 g) |
| --- | --- |
| Primycin-NMP basic gel (20%) | 5.00 |
| Alcohol cetylicus | 5.00 |
| Emulsifier E 2155 (T. Goldschmidt, Essen, GFR) | 5.00 |
| Spiritus concentrallissimus | 5.00 |
| Distilled water ad | 100.00 |

The cetyl alcohol, emulsifier E 2555 (stearilic alcohol polyglycol ether; manufacturer: T. Goldschmidt, Essen, GFR) and a major part of the distilled water are melt on a water-bath at 60°–70° C. under constant stirring. The primycin-NMP basic gel and the concentrated alcohol are added in portions under constant stirring whereupon it is filled up with distilled water.

EXAMPLE 16

"For the Night Use" Cream

| Component | Amount (to 100 g) |
| --- | --- |
| Primycin-NMP basic gel (20%) | 5.00 |
| Alcohol cetyl stearilicus | 3.15 |
| Stearinum | 7.00 |
| Sodium lauryl sulfuricum | 0.35 |
| Solution conservans (Ph.Hg.VI.) | 0.70 |
| Solitolum | 2.45 |
| Glycerol | 30.00 |
| Distilled water ad | 100.00 |

The components of the basic ointment are melted at 65°–70° C. on a water-bath under constant stirring whereupon the primycin-NMP basic gel is added under further stirring and the cream is filled up with distilled water.

EXAMPLE 17

Dusting Powder Comprising Primycin

| Component | Amount (g) |
| --- | --- |
| Primycin-NMP basic gel (20%) | 10.00 |
| Zinc oxide | 40.00 |
| Talc | 50.00 |

The zinc oxide is thoroughly mixed with the talc and sieved through a VI. mesh sieve. The powder mixture is homogenized with the primycin-NMP gel and dried in an exsiccator at 40° C. for 24 hours. The dried powder mixture thus obtained is sieved (VI. sieve, mesh 0.16 mm) and homogenized. Thus a white homogenous powder mixture is obtained.

EXAMPLE 18

Dusting Powder Comprising Primycin

| Component | Amount (g) |
| --- | --- |
| Primycin-NMP basic gel (20%) | 10.00 |
| N,N-dimethyl-acetamide | 5.00 |
| Zinc oxide | 40.00 |
| Talc | 45.00 |

The primycin-NMP basic gel is dissolved in N,N-dimethyl-acetamide under warming and the warm solution is sprayed onto a zinc oxide-talc powder mixture prepared according to Example 15. The sprayed powder mixture is kept in an essiccator for 24 hours at 40° C. and sieved (sieve No. VI, mesh 0.16 mm) and finally homogenized. Thus a white homogeneous powder mixture is obtained.

EXAMPLE 19

Mixed Basic Gel Comprising Primycin+Gentamycin

| Component | Amount (for 100.00 g) |
| --- | --- |
| Primycin-NMP basic gel (20%) | 50.00 |
| Gentamycin sulfate | 20.00 |
| Distilled water | 30.00 |

The gentamycin sulfate is dissolved in distilled water on an oil-bath having a temperature of 40° C. whereupon the primycin-NMP basic gel is added at this temperature. A transparent clear solution is obtained which turns at room temperature within 24 hours to a glasslike transparent gel. The mixed basic gel obtained comprises 10% of primycin and 20% of gentamycin.

EXAMPLE 20

Mixed Basic Gel Comprising Primycin and Doxicyclin

| Component | Amount (for 100.00 g) |
| --- | --- |
| Primycin-NMP basic gel (20%) | 50.00 |
| Doxicyclin | 20.00 |
| Distilled water | 30.00 |

The doxicyclin is dissolved in distilled water on a water-bath having a temperature of 40° C. whereupon the primycin-NMP basic gel is added at the above temperature. A water-clear transparent solution is obtained, which turns at room temperature within 24 hours to a glasslike transparent gel.

The mixed basic gel thus obtained comprises 10% of primycin and 20% of doxycyclin.

EXAMPLE 21

Composition for the Treatment of Mastitis in the Lactation Period

| Component | Amount (for 100.00 g) |
| --- | --- |
| Mixed basic gel comprising primycin and gentamycin | 10.00 |

-continued

| Component | Amount (for 100.00 g) |
|---|---|
| Emulsifier E 2209 (T. Goldschmidt, Essen, GFR) | 5.00 |
| Procaine-hydrochloride | 1.60 |
| Distilled water ad | 100.00 |

To an aqueous solution of the procain hydrochloride the Emulsifier E 2209 (cetyl alcohol polyglycol ether, manufacturer: T. Goldschmidt, Esser, GFR) is added whereupon the primycin-gentamycin basic gel is added under constant stirring.

Thus a paste-like composition suitable for the treatment of mastitis is obtained.

EXAMPLE 22

Composition for the Treatment of Mastitis in the Dry Period

| Component | Amount (for 100.00 g) |
|---|---|
| Mixed basic gel comprising primycin and gentamycin | 10.00 |
| Tagat R-40 (T. Goldschmidt, Essen, GFR) | 5.00 |
| Ung. Simplex | 35.00 |
| Glycerol | 50.00 |

Composition of Unguentum Simplex (Ph. g. VI)

| Component | Amount (for 100 g) |
|---|---|
| Lanalcolum | 6.00 |
| Alcohol cetyl stearilicus | 3.00 |
| Vaselinum album ophthalmicum | 12.00 |
| Vaselinum album | 79.00 |

The Ung. simplex and Tagat R-40 (T. Goldschmidt, Essen, GFR) are added to glycerol, whereupon a mixed basic gel comprising primycin and gentamycin is added under constant stirring.

Thus a paste-like composition suitable for the treatment of mastitis is obtained.

EXAMPLE 23

Composition for the Treatment of Mastitis in the Dry Period

| Component | Amount (for 100 g) |
|---|---|
| Mixed basic gel comprising primycin and gentamycin | 10.00 |
| Emulsifier E 2209 (T. Goldschmidt, Essen, GFR) | 5.00 |
| Ung. simplex | 30.00 |
| Oleum helianthi | 55.00 |

The Emulsifier E 2209 (cetyl alcohol polyglycol ether, manufacturer: T. Goldschmidt, Essen, GFR) is melted on a water-bath and homogenized with Unguentum simplex. The basic gel comprising primycin and gentamycin is uniformly dispersed in the cold, whereupon the sunflower oil is added in portions.

EXAMPLE 24

Composition for the Treatment of Mastitis in the Dry Period

| Component | Amount (100.00 g) |
|---|---|
| Mixed basic gel comprising primycin and doxicyclin | 10.00 |
| Tagat R-40 (T. Goldschmidt, Essen, GFR) | 5.00 |
| Ung. simplex | 35.00 |
| Glycerol | 50.00 |

The Unguentum simplex and Tagat R-40 (T. Goldschmidt, Essen, GFR) are added to the glycerol, whereupon the basic gel comprising primycin and doxycycline is added under constant stirring.

Thus a past-like formulation suitable for the treatment of mastitis is obtained.

A principal part of the invention is that the new primycin-containing colloidal basic gel can be topically applied to the skin of a patient suffering from acne to successfully treat the disease without any irritating side effects. Normally primycin is an irritant and cannot be topically administered to a patient without causing severe irritation to the skin.

An advantage of the presently disclosed compositions is that primycin may be topically applied to an acne patient. Primycin when topically applied according to the presently claimed invention has been found not to be absorbed by the blood stream. Since primycin can be significantly toxic upon entry into the bloodstream, this topical administration as opposed to enteral administration or administration by injection is highly preferable.

While the primycin gel according to the present invention applied topically does not enter the bloodstream, nonetheless the primycin is effectively delivered to the skin of the patient because the gel formed is highly stable making the new composition highly effective in treating acne. We know of no other topical form of primycin that is so effective in topical treatment of acne since it is very difficult indeed to even solubilize primycin, let alone provide a stable primycin-containing composition for topical use.

TESTS

1. The primycin-sulphate antibiotics tested by us many times are practically insoluble at room temperature in the physiologically acceptable solvents e.g. water, ethanol, methanol, propylene glycol, isopropylene glycol, isopropyl alcohol, ethylene-diamene, acetone, isopropyl myristate (see Table A). 1% solutions were prepared with the above solvents under heating, from which mixtures primycin precipitated upon cooling and the solutions being clear while hot turned into cloudy suspensions. The aqueous suspension was agitated and filtered, the primycin content of the filtrate was determined by microbiological methods.

2. Possible absorption and irritating effect of a basic gel of 20% primycin content and of a cream containing 5% basic gel was tested on New Zealand rabbits
   a) No primycin is absorbed from the complex, in the blood no inhibiting effect can be observed.

This result is remarkable since in the form of NMP solutions absorption is possible or even promoted, but for gel complexes this observation is not valid.
   b) It has no local irritating effect on the body.

TABLE A

| Solubility of primycin sulphate at 20° C. | |
|---|---|
| Solvent | Dissolved material mg/ml |
| water | 0.000050 |
| methanol | 0.002000 |
| propylene glycol | 0.005000 |

HISTOPATHOLOGICAL EXAMINATION OF THE SKIN IRRITATING EFFECT OF PRIMYCIN OINTMENT AND GEL IN RABBITS TREATED DERMALLY OVER 5 DAYS

Examinations were performed on 40 New Zealand rabbits.

In experiment I. in depilated, in experiment II. in depilated and scarified animals. Skin of the animals treated for 5 days with primycin containing ointments (samples 1 and 2) and gel (sample 3) as well as with ointment vehicle in histological sections stained with Haematoxylin eosin.

Alterations Observed

Experiment I

Sample 1

The skin is usually slightly wrinkled (rabbit 5), epithelium is thickened in a circumscribed area in three animals (rabbits 1, 2, 5); with squamous keratinized layers on the skin surface in two animals (rabbits 3, 5).

Sample 2

In three animals (rabbits 8, 11, 12) the skin is slightly wrinkled and the epithelium is thickened in small areas. In one animal (rabbit 8) a pin-prick sized epithelial defect is filled with erythrocytes and lymphoid cells. In 2 animals (rabbits 8, 12) the epithelium is covered by crust.

Sample 3

In three animals (rabbits 13, 16, 18) the epithelium is thickened and covered by a thin crust containing large amounts of cellular elements in one animal. Cutis and subcutaneous connective tissue are intact.

Experiment II

Sample 1

In three animals (rabbits 19, 21, 24) small areas of the epithelium are thickened; in one animal the epithelium is thickened by squamous keratinization. Cutis and subcutis are intact.

Sample 2

In one animal (rabbit 28), a pin-prick sized epithelial defect is filled by accumulated erythrocytes and lymphoid cells. In two animals (rabbits 28, 30) small areas of the epithelium are thickened, covered by thin crust.

Sample 3

In three animals (rabbits 31, 33, 35) small areas of the epithelium are thickened and covered by thin crust. In one animal (rabbit 31) the crust contains abundant amount of cellular elements. Cutis and subcutis are intact.

Control

1. Depilated skin of the animals treated with ointment vehicle is intact.

2. In the scarified group treated with ointment vehicle in one animal (rabbit 40) a small area of the epithelium is thickened, cutis and subcutis are intact.

The above described method of examination did not reveal any alteration attributable to the compound under study.

The slight structural changes localized in small areas remained within the physiological limits: they were signs of regeneration after depilation (thickening of the epithelium and to scarification (crusts). No alterations were found in the cutis and subcutaneous connective tissue.

Structural changes extending to somewhat larger areas found in some animals of the group treated with Sample 3 are explained by the skin drying effect of the jelly.

EXAMINATION OF THE LOCAL IRRITANT EFFECT AND ABSORPTION OF PRIMYCIN SAMPLES IN THE RABBIT

Purpose of the Study

Examination of the absorption and local irritant effect of primycin in the rabbit, at dermal application.

Samples Tested

Sample 1—manufact. No. K 02 02 86
Sample 2—manufact. No. K 01 02 86
Sample 3—manufact. No. 1.2. K-30286
Sample 4—ointment vehicle without active material Dose 0.5 g sample/animal/day Animals New Zealand rabbits Duration of the Study 5 days Assassmant of primycin Microbiological assay with agar diffusion technique using Bacillus subtilis.

Date of the Study

From Mar. 11 to 26, 1986.

Protocol

Compiled by Jenó Marton M.D., on Feb. 24, 1986.

I. TEST SUBSTANCES

Sample 1

1% gel containing 20% primycin and 80% N-methyl pyrrolidine-2-one, 99% ointment vehicle
Batch No.: K 02 02 86

Sample 2

5% gel containing 20% primycin and 80% N-methyl-pyrrolidine-2-one, 90% ointment vehicle
Batch No.: K 01 02 86

Sample 3

Gel containing 20% primycin and 80% N-methyl-pyrrolidine-2-one
Batch No.: 1.2. K-30286

Sample 4

Ointment vehicle without active substance.

II. METHODS

1. Experimental Animals

Studies were performed on New Zealand rabbits of MD hygienic category. Males and females were used in 1:1 ratio.

Bodyweight of the animals, at the beginning of the study, was around 2500 g.

Keeping Conditions

The animals were kept in individual cages at an ambient temperature of 20° to 22° C., 70% relative humidity and 12 hours alternating light and dark periods.

Feeding

Animals were fed a standard compressed rabbit food (Környe, State farm) and had access to water ad libitum.

Before the beginning of the study the animals were kept under observation for one week (quarantine). Healthy rabbits displaying no pathological clinical symptoms were used in the study.

Animals were randomized using the random numbers of the table in "Handbook of Tables for Probability and Statistics" (CRC Press, Inc., Florida).

Identification

By ear numbers.

2. Grouping, Number of Animals

| Groups | | Test substances | Number of animals male/female | Identification numbers males/females |
|---|---|---|---|---|
| studies on the intact skin | 1 | Sample 1 | 3/3 | 1-3/4-6 |
| | 2 | Sample 2 | 3/3 | 7-9/10-12 |
| | 3 | Sample 3 | 3/3 | 13-15/16-18 |
| studies on the scarified skin | 4 | Sample 1 | 3/3 | 19-21/22-24 |
| | 5 | Sample 2 | 3/3 | 25-27/28-30 |
| | 6 | Sample 3 | 3/3 | 31-33/34-36 |
| intact skin | 7 | Sample 4 | 1/1 | 36/38 |
| scarified skin | 8 | Sample 4 | 1/1 | 29/40 |

3. Experimental Arrangement

| Days | 0 | 1 | 2 | 3 | 4 | 5 | 6 |
|---|---|---|---|---|---|---|---|
| Depilation | + | | | | | | |
| Scarification | + | | | | | | |
| Treatment | | + | + | + | + | + | |
| Blood sampling and assessment | + | + | + | + | + | + | |
| Observation of skin irritation | | | + | + | + | + | + |
| Autopsy | | | | | | | + |

4. Treatment

4.1. Depilation

A 2.5×3 cm area of the dorsal skin of the rabbit was depilated on the day prior to treatment.

4.2. Scarification

Animals belonging to groups 4, 5, 6 and 8 were scarified in the depilated area so that 10 to 12 longitudinal scratches were made to the depth of the stratum corneum without causing haemorrhage.

4.3. Application of the Samples

Twenty-four hours after depilation or scarification 0.5 g of the test samples was applied to the depilated or scarified area of the dorsal skin of the rabbit, once daily. The treated areas were covered by water proof gauze coated surgical plasters.

The plaster was removed after 24 hours and the treated areas were cleaned from the ointment residue of the previous treatment. Treatments were repeated on 5 consecutive days.

4.4. Blood Sampling

Blood samples were taken on days 0, 1, 2, 3, 4 and 5 from the marginal vein of the ear once daily, three hours after the application of the ointment.

5. Examinations Performed

5.1. Lethality

Recorded daily.

5.2. Clinical Symptoms

After treatment the animals were kept under continuous observation for three hours and their behaviour and toxic symptoms, if any, were recorded.

5.3. Examination of Local Irritant Effect

Assessment of the local irritant effect was made according to two principal aspects: the development of erythema and edema. However, any other alteration observed on the treated skin surface was also recorded.

Assessment of Erythema and Crust Formation

| | scores |
|---|---|
| no skin alteration | 0 |
| very slight erythema | 1 |
| well defined erythema | 2 |
| moderately severe erythema | 3 |
| severe erythema with intensive skin discoloration, with crust formation into the depth | 4 |

Assessment of Edema

| | |
|---|---|
| no edema | 0 |
| very slight edema | 1 |
| slight edema (with well defined contours) | 2 |
| moderate edema (cca 1 mm protuberance) | 3 |
| severe edema (with more than 1 mm protuberance occurring even beyond the treated area) | 4 |

5.4. Microbiological Determination of Primycin Concentration in the Serum

Principle of the Method

Serum primycin concentrations were determined by agar diffusion technique. The assessment was performed according to USP XXI Biological Tests and Assays.

Performance of the Method

Test organism: Suspension of Bacillus subtilis (ATCC 6633) spore, deriving from DIFCO Laboratories B-0453-36.

Culture Medium

Bacto Antibiotic Medium 2 (DIFCO B-0270).

Measurements were made on one layer agar plates prepared in Petri dishes of 9 cm diameter. Each Petri dish was filled with 10 ml culture medium, previously mixed with the spore suspension.

Preparation of Spore Suspension and Adjustment of the Spore Count in the Culture Medium DIFCO spore suspension obtained in 1 ml ampoules were kept at 70° to 80° C. for 40 min to kill the vegetative cells and then the spore count of the culture medium was adjusted to $5 \times 10^5$ per ml by counting under the microscope in a bacterium counting chamber.

Preparation of the Petri Dishes

Petri dishes used for the study were placed on horizontally adjusted plates and were filled with 10 ml culture medium containing the above described spore suspension and the plates prepared in this way were stored.

Storage

At +4° C. at least for 30 min.

After storage at +4° C. 6 holes of 9 mm diameter were made with a punch into each plate. These holes were to contain identical volumes of standard primycin concentrations and the serum to be tested.

Primycin Standard

Origin and Identification of the Standard

The standard was provided by Chinoin Pharmaceutical and Chemical Works Ltd. Code: primycin II 1978.XXI.950 U/mg.

Measurement and Preparation of the Standard for the Stock Solution 0.1 g primycin is weighed with ±0.001 g accuracy. It is exsiccated in vacuo (5 torr) at 60° C. for 3 hours. After exsiccation the standard is weighed again.

Dissolution of the standard: the exactly known amount of primycin is dissolved in 500 ml BEW (butanol:ethanol:water, 1:1:2). Concentration of this solution is computed. This is the stock solution of the standard which when stored at 4° C., can be used for one month at the maximum.

Preparation of Standard Concentrations for the Measurements

The standard stock solution was diluted to 10 μg/ml concentration with sterile distilled water and further dilutions were always made with freshly prepared rabbit serum.

Standard Concentrations Applied

For each series of measurement (each day) a concentration series of 5-2-1.5-1.0-0.75-0.5 μg/ml was prepared. 9 parallel measurements were made. Dilutions of the standard series are shown in Table 3.

Weighing in of the Standard

From each standard concentration a volume of 50 μl was filled into each hole by the use of a 50 μl automatic pipette of Nichiryo Model 800.

Preparation and Assessment of the Samples with Unknown Primycin Content

Blood samples were centrifuged at 2000 rpm for 30 min using a Janetzky T23 centrifuge. From the obtained serum 50 μl volumes were filled into the holes of 9 mm diameter of the prepared Petri dishes. The unknown samples were distributed into the individual Petri dishes according to the random pattern described in USP XXI.

Incubation

At 37°±0.5° C. for 16 to 20 hours.

Evaluation of the Zones of Extinction

Diameter of extinction zones formed during the incubation time were determined by a measuring device. The results were evaluated by a Commodore 64 microcomputer. Sensitivity of the method: 0.5 μg/ml.

Quality Control

On the days of examination samples "unknown" for the staff were also processed. Concentration of this sample was 0.8 μg/ml. Mean value of the measured concentrations was: 0.78±0.11 μg/ml.

5.5. Autopsy and Histology

At the end of the study all animals were killed by intravenous injection of hypersaturated magnesium sulphate solution. The treated skin areas were removed and after fixation in 10% formalin they were submitted to histological processing.

5.6. Duration of the Study

From Mar. 16 to Mar. 21, 1986.

III. RESULTS

1. Lethality

During the study no animal of any of the treated groups had died.

2. Clinical Symptoms

During the examination period no pathological clinical or toxic symptoms were observed.

3. Local Irritant Effect

Detailed results of skin alterations observed during the 5 consecutive days are demonstrated in Tables 1 and 2.

Samples 1 and 2 applied for 5 consecutive days *caused no local irritation* on either the intact or the scarified skin surface. It must be mentioned, however, that in rabbits 5, 8, 9, 21 and 24 slight erythema developed, possibly due to the following causes: during the 24-hour exposition the large amount (0.5 g) of ointment applied to the small skin area dried up to form a crust-like layer and caused mechanical injury of the skin.

Under the effect of the ointment the skin got exsiccated and, as a consequence cracked which led to the observed alterations. As these changes took place only in some of the animals, they may be related to individual sensitivity.

*Applied to the intact skin* sample 3 caused 48 hours after the first application well defined erythema with squamous crusts in each animal. By the end of the study these alterations improved and epithelial regeneration began. It deserves attention that these alterations were more prominent in the males than in the females.

*Applied to the scarified skin* sample 3 caused alterations in the male animals. The observed symptoms were identical with those found on the intact skin.

No alterations were seen in the females. Summing up, it can be stated that sample 3 applied to the intact depilated skin surface caused *more or less severe skin alterations in both the males and females.*

The observed symptoms were aggravated by the fact that the gel sample 3 had completely dried within 24 hours and caused mechanical injury to the desiccated skin.

In the control group (groups 7 and 8) no alteration was observed either on the intact or on the scarified skin.

Hair growth was not affected by the applied substances.

The above alterations will be confirmed by autopsy and histopathology.

4. Examination of the Absorption of Primycin

Serum primycin concentrations were determined on days 0, 1, 2, 3, 4 and 5 of the study. Standard series prepared daily are shown in Tables 4, 5 and 6. The individual tables contain the applied primycin concentrations in μg/ml, diameters of the extinction zones in mm, as well as the parameters of the calibration curve.

In the sera of the treated animals *no primycin concentration could be detected* at the tested points of time by the applied method (Table 7).

5. Autopsy and Histopathology

Results of the autopsy are included hereinafter.

TABLE 1

Examination of the local irritant effect
(individual data)
Irritant effect after the first application
Er = erythema; Ed = edema

| | No of the animal | 24 hours Er | 24 hours Ed | 48 hours Er | 48 hours Ed | 72 hours Er | 72 hours Ed | 96 hours Er | 96 hours Ed | 120 hours Er | 120 hours Ed |
|---|---|---|---|---|---|---|---|---|---|---|---|
| 1 | 1. | 0 | 0 | 0 | 0 | 0 | 0 | 0 | 0 | 0 | 0 |
| | 2. | 0 | 0 | 0 | 0 | 0 | 0 | 0 | 0 | 0 | 0 |
| | 3. | 0 | 0 | 0 | 0 | 0 | 0 | 0 | 0 | 0 | 0 |
| | 4. | 0 | 0 | 0 | 0 | 0 | 0 | 0 | 0 | 0 | 0 |
| | 5. | 0 | 0 | 0 | 0 | 1 | 0 | 1 | 0 | 1 | 0 |
| | 6. | 0 | 0 | 0 | 0 | 0 | 0 | 0 | 0 | 0 | 0 |
| 2 | 7. | 0 | 0 | 0 | 0 | 0 | 0 | 0 | 0 | 0 | 0 |
| | 8. | 0 | 0 | 0 | 0 | 2 | 0 | 2 | 0 | 1 | 0 |
| | 9. | 0 | 0 | 0 | 0 | 0 | 1 | 1 | 0 | 0 | 0 |
| | 10. | 0 | 0 | 0 | 0 | 0 | 0 | 0 | 0 | 0 | 0 |
| | 11. | 0 | 0 | 0 | 0 | 0 | 0 | 0 | 0 | 0 | 0 |
| | 12. | 0 | 0 | 0 | 0 | 0 | 0 | 0 | 0 | 0 | 0 |
| 3 | 13. | 1 | 0 | 2 | 1 | 1 | 0 | 1 | 0 | 1 | 0 |
| | 14. | 3 | 0 | 2 | 0 | 1 | 0 | 1 | 0 | 1 | 0 |
| | 15. | 3 | 1 | 3 | 0 | 2 | 0 | 1 | 0 | 1 | 0 |
| | 16. | 1 | 0 | 2 | 0 | 1 | 0 | 1 | 0 | 1 | 0 |
| | 17. | 0 | 0 | 2 | 0 | 1 | 0 | 0 | 0 | 0 | 0 |
| | 18. | 0 | 0 | 2 | 0 | 1 | 0 | 1 | 0 | 0 | 0 |
| 4 | 19. | 0 | 0 | 0 | 0 | 0 | 0 | 0 | 0 | 0 | 0 |
| | 20. | 0 | 0 | 0 | 0 | 0 | 0 | 0 | 0 | 0 | 0 |
| | 21. | 2 | 0 | 1 | 0 | 0 | 0 | 0 | 0 | 0 | 0 |
| | 22. | 0 | 0 | 0 | 0 | 0 | 0 | 0 | 0 | 0 | 0 |
| | 23. | 0 | 0 | 0 | 0 | 0 | 0 | 0 | 0 | 0 | 0 |
| | 24. | 1 | 0 | 1 | 0 | 1 | 0 | 0 | 0 | 0 | 0 |
| 5 | 25. | 0 | 0 | 0 | 0 | 0 | 0 | 0 | 0 | 0 | 0 |
| | 26. | 0 | 0 | 0 | 0 | 0 | 0 | 0 | 0 | 0 | 0 |
| | 27. | 0 | 0 | 0 | 0 | 0 | 0 | 0 | 0 | 0 | 0 |
| | 28. | 0 | 0 | 0 | 0 | 0 | 0 | 0 | 0 | 0 | 0 |
| | 29. | 0 | 0 | 0 | 0 | 0 | 0 | 0 | 0 | 0 | 0 |
| | 30. | 0 | 0 | 0 | 0 | 0 | 0 | 0 | 0 | 0 | 0 |
| 6 | 31. | 3 | 1 | 2 | 1 | 1 | 0 | 1 | 0 | 1 | 0 |
| | 32. | 0 | 0 | 1 | 0 | 1 | 0 | 1 | 0 | 1 | 0 |
| | 33. | 3 | 0 | 2 | 0 | 2 | 0 | 2 | 0 | 2 | 0 |
| | 34. | 0 | 0 | 0 | 0 | 0 | 0 | 0 | 0 | 0 | 0 |
| | 35. | 0 | 0 | 0 | 0 | 0 | 0 | 0 | 0 | 0 | 0 |
| | 36. | 0 | 0 | 0 | 0 | 0 | 0 | 0 | 0 | 0 | 0 |
| 7 | 37. | 0 | 0 | 0 | 0 | 0 | 0 | 0 | 0 | 0 | 0 |
| | 38. | 0 | 0 | 0 | 0 | 0 | 0 | 0 | 0 | 0 | 0 |
| 8 | 39. | 0 | 0 | 0 | 0 | 0 | 0 | 0 | 0 | 0 | 0 |
| | 40. | 0 | 0 | 0 | 0 | 0 | 0 | 0 | 0 | 0 | 0 |

TABLE 2

Examination of the local irritant effect
(individual data)

| No | 24 | 48 | 72 | 96 | 120 | 24 | 48 | 72 | 96 | 120 | Average |
|---|---|---|---|---|---|---|---|---|---|---|---|
| | Edema | | | | | Erythema | | | | | |
| 1 | 0 | 0 | 0 | 0 | 0 | 0 | 0 | 0 | 0 | 0 | .0 |
| 2 | 0 | 0 | 0 | 0 | 0 | 0 | 0 | 0 | 0 | 0 | .0 |
| 3 | 0 | 0 | 0 | 0 | 0 | 0 | 0 | 0 | 0 | 0 | .0 |
| 4 | 0 | 0 | 0 | 0 | 0 | 0 | 0 | 0 | 0 | 0 | .0 |
| 5 | 0 | 0 | 0 | 0 | 0 | 0 | 0 | 1 | 1 | 1 | .3 |
| 6 | 0 | 0 | 0 | 0 | 0 | 0 | 0 | 0 | 0 | 0 | .0 |
| | | | | | | | | Group average = | | | .05 P(T) = .138 |
| 7 | 0 | 0 | 0 | 0 | 0 | 0 | 0 | 0 | 0 | 0 | .0 |
| 8 | 0 | 0 | 0 | 0 | 0 | 0 | 0 | 2 | 2 | 1 | .5 |
| 9 | 0 | 0 | 0 | 0 | 0 | 0 | 0 | 0 | 1 | 0 | .1 |
| 10 | 0 | 0 | 0 | 0 | 0 | 0 | 0 | 0 | 0 | 0 | .0 |
| 11 | 0 | 0 | 0 | 0 | 0 | 0 | 0 | 0 | 0 | 0 | .0 |
| 12 | 0 | 0 | 0 | 0 | 0 | 0 | 0 | 0 | 0 | 0 | .0 |
| | | | | | | | | Group average = | | | .1 P(T) = .11 |
| 13 | 0 | 1 | 0 | 0 | 0 | 1 | 2 | 1 | 1 | 1 | .7 |
| 14 | 0 | 0 | 0 | 0 | 0 | 3 | 2 | 1 | 1 | 1 | .8 |
| 15 | 1 | 0 | 0 | 0 | 0 | 3 | 3 | 2 | 1 | 1 | 1.1 |
| 16 | 0 | 0 | 0 | 0 | 0 | 1 | 2 | 1 | 1 | 1 | .6 |
| 17 | 0 | 0 | 0 | 0 | 0 | 0 | 2 | 1 | 0 | 0 | .3 |
| 18 | 0 | 0 | 0 | 0 | 0 | 2 | 1 | 1 | 0 | | .4 |
| | | | | | | | | Group average = | | | .65 P(T) < 0.01 |
| 19 | 0 | 0 | 0 | 0 | 0 | 0 | 0 | 0 | 0 | 0 | .0 |
| 20 | 0 | 0 | 0 | 0 | 0 | 0 | 0 | 0 | 0 | 0 | .0 |

TABLE 2-continued

Examination of the local irritant effect
(individual data)

| No | Scores after 24 | 48 | 72 | 96 | 120 | 24 | 48 | 72 | 96 | 120 | Average |
|----|----|----|----|----|----|----|----|----|----|----|---------|
|    | Edema | | | | | Erythema | | | | | |
| 21 | 0 | 0 | 0 | 0 | 0 | 2 | 1 | 0 | 0 | 0 | .3 |
| 22 | 0 | 0 | 0 | 0 | 0 | 0 | 0 | 0 | 0 | 0 | .0 |
| 23 | 0 | 0 | 0 | 0 | 0 | 0 | 0 | 0 | 0 | 0 | .0 |
| 24 | 0 | 0 | 0 | 0 | 0 | 1 | 1 | 1 | 0 | 0 | .3 |
|    | | | | | | | | | Group average = | | .1 P(T) = .08 |
| 25 | 0 | 0 | 0 | 0 | 0 | 0 | 0 | 0 | 0 | 0 | .0 |
| 26 | 0 | 0 | 0 | 0 | 0 | 0 | 0 | 0 | 0 | 0 | .0 |
| 27 | 0 | 0 | 0 | 0 | 0 | 0 | 0 | 0 | 0 | 0 | .0 |
| 28 | 0 | 0 | 0 | 0 | 0 | 0 | 0 | 0 | 0 | 0 | .0 |
| 29 | 0 | 0 | 0 | 0 | 0 | 0 | 0 | 0 | 0 | 0 | .0 |
| 30 | 0 | 0 | 0 | 0 | 0 | 0 | 0 | 0 | 0 | 0 | .0 |
|    | | | | | | | | | Group average = | | .0 P(T) = 1 |
| 31 | 1 | 1 | 0 | 0 | 0 | 3 | 2 | 1 | 1 | 1 | 1.0 |
| 32 | 0 | 0 | 0 | 0 | 0 | 0 | 1 | 1 | 1 | 1 | .4 |
| 33 | 0 | 0 | 0 | 0 | 0 | 3 | 2 | 2 | 2 | 2 | 1.1 |
| 34 | 0 | 0 | 0 | 0 | 0 | 0 | 0 | 0 | 0 | 0 | .0 |
| 35 | 0 | 0 | 0 | 0 | 0 | 0 | 0 | 0 | 0 | 0 | .0 |
| 36 | 0 | 0 | 0 | 0 | 0 | 0 | 0 | 0 | 0 | 0 | .0 |
|    | | | | | | | | | Group average = | | .42 P(T) < 0.01 |

TABLE 3

Standard dilution series

| Dilution series | Conc. μg/ml | Measured volume (ml) of stock solution of 0.10 μg/ml | Measured volume (ml) of serum |
|---|---|---|---|
| 1 | 5 | 1.000 | 1.000 |
| 2 | 2 | 1.000 | 4.000 |
| 3 | 1.5 | 0.375 | 2.125 |
| 4 | 1 | 0.500 | 4.500 |
| 5 | 0.75 | 0.1875 | 2.3125 |
| 6 | 0.5 | 0.250 | 4.750 |

TABLE 4

Examination of dermal absorption of primycin

Concentrations: (μg/ml)

| | 5.00 | 2.00 | 1.50 | 1.00 | .75 | .50 |
|---|---|---|---|---|---|---|
| Biol. titration. Primycin standard curve: 860316-17 | | | | | | |
| Extinction zones (mm) | | | | | | |
| 1 | 19.2 | 16.0 | 14.8 | 13.6 | 12.7 | 11.4 |
| 2 | 18.9 | 16.3 | 15.2 | 14.2 | 12.6 | 11.4 |
| 3 | 19.0 | 16.3 | 14.9 | 13.7 | 12.6 | 11.3 |
| 4 | 19.3 | 16.0 | 14.9 | 14.1 | 12.5 | 10.8 |
| 5 | 18.9 | 15.8 | 14.7 | 13.3 | 12.4 | 11.2 |
| 6 | 19.2 | 16.3 | 15.6 | 14.5 | 12.7 | 11.0 |
| 7 | 19.1 | 16.3 | 14.8 | 13.9 | 12.5 | 10.9 |
| 8 | 19.1 | 16.0 | 15.2 | 14.6 | 12.6 | 10.9 |
| 9 | 19.7 | 16.6 | 15.2 | 13.9 | 12.1 | 10.9 |

Parameters of the calibration curve:
slope: 3.49282552
section of the axis: 13.653779
correlation coeff.: .99280883

| Biol. titration. Primycin standard curve: 860317-18 | | | | | | |
|---|---|---|---|---|---|---|
| Extinction zones (mm) | | | | | | |
| 1 | 20.1 | 16.0 | 14.8 | 13.6 | 12.8 | 11.2 |
| 2 | 20.2 | 16.3 | 15.2 | 13.4 | 12.3 | 11.2 |
| 3 | 20.3 | 16.5 | 15.2 | 14.0 | 12.8 | 11.4 |
| 4 | 19.8 | 16.0 | 15.0 | 13.6 | 12.5 | 11.1 |
| 5 | 19.8 | 16.0 | 14.7 | 13.3 | 12.6 | 11.1 |
| 6 | 19.8 | 16.2 | 15.2 | 13.8 | 12.4 | 11.0 |
| 7 | 20.1 | 16.0 | 15.1 | 13.8 | 12.6 | 11.2 |
| 8 | 20.1 | 16.1 | 15.3 | 14.1 | 12.5 | 11.0 |
| 9 | 20.2 | 16.2 | 15.2 | 13.8 | 12.4 | 11.3 |

Parameters of the calibration curve:
slope: 3.84243708
section of the axis: 13.6753585
correlation coeff.: .996700484

TABLE 5

Dermal absorption of primycin

Concentrations: (μg/ml)

| | 5.00 | 2.00 | 1.50 | 1.00 | .75 | .50 |
|---|---|---|---|---|---|---|
| Biol. titration. Primycin standard curve: 860318-19 | | | | | | |
| Extinction zones: (mm) | | | | | | |
| 1 | 19.6 | 15.5 | 14.8 | 13.2 | 11.5 | 10.3 |
| 2 | 19.7 | 15.5 | 14.5 | 12.5 | 11.2 | 9.8 |
| 3 | 19.5 | 15.9 | 14.5 | 13.4 | 11.4 | 10.1 |
| 4 | 19.6 | 15.5 | 14.5 | 13.1 | 11.6 | 9.8 |
| 5 | 19.5 | 15.5 | 14.5 | 12.5 | 11.1 | 7.9 |
| 6 | 19.8 | 15.8 | 15.0 | 13.2 | 12.2 | 10.0 |
| 7 | 19.6 | 15.2 | 14.1 | 13.0 | 11.5 | 10.2 |
| 8 | 19.1 | 15.3 | 14.5 | 13.5 | 11.8 | 9.8 |
| 9 | 19.8 | 15.5 | 14.0 | 12.5 | 11.3 | 10.0 |

Parameters of the calibration curve:
slope: 4.21743237
section of the axis: 12.761853
correlation coeff.: .991989122

TABLE 6

Examination of dermal absorption of primycin

Concentrations (μg/ml)

| | 5.00 | 2.00 | 1.50 | 1.00 | .75 | .50 |
|---|---|---|---|---|---|---|
| Biol. titration. Primycin standard curve: 860319-20 | | | | | | |
| Extinction zones: (mm) | | | | | | |
| 1 | 19.6 | 15.5 | 14.8 | 13.2 | 11.5 | 10.3 |
| 2 | 19.6 | 15.5 | 14.5 | 13.1 | 11.6 | 9.8 |
| 3 | 19.6 | 15.2 | 14.1 | 13.0 | 11.5 | 10.2 |
| 4 | 19.8 | 15.5 | 14.0 | 12.5 | 11.3 | 10.0 |
| 5 | 19.7 | 15.5 | 14.5 | 12.5 | 11.2 | 9.8 |
| 6 | 19.5 | 15.5 | 14.5 | 12.5 | 11.1 | 9.9 |
| 7 | 19.1 | 15.3 | 14.5 | 13.5 | 11.8 | 9.8 |

TABLE 6-continued

| Examination of dermal absorption of primycin | | | | | | |
|---|---|---|---|---|---|---|
| | Concentrations (μg/ml) | | | | | |
| | 5.00 | 2.00 | 1.50 | 1.00 | .75 | .50 |
| 8 | 19.5 | 15.2 | 14.5 | 13.3 | 11.9 | 9.8 |
| 9 | 19.5 | 15.9 | 14.5 | 13.4 | 11.4 | 10.1 |

Parameters of the calibration curve:
slope: 4.13933195
section of the axis: 12.7880395
correlation coeff.: .995813434

| Biol. titration. Primycin standard curve: 860320-21 | | | | | | |
|---|---|---|---|---|---|---|
| Extinction zones: (mm) | | | | | | |
| 1 | 19.8 | 16.5 | 15.2 | 13.6 | 12.7 | 11.9 |
| 2 | 19.6 | 16.0 | 14.8 | 13.0 | 12.6 | 11.4 |
| 3 | 19.6 | 16.1 | 15.3 | 13.9 | 12.5 | 11.0 |
| 4 | 19.8 | 16.3 | 15.2 | 13.8 | 12.5 | 11.4 |
| 5 | 19.7 | 15.7 | 14.8 | 13.5 | 12.5 | 11.6 |
| 6 | 19.7 | 16.0 | 15.1 | 13.6 | 12.2 | 11.2 |
| 7 | 19.6 | 16.3 | 15.0 | 13.6 | 12.5 | 11.5 |
| 8 | 19.7 | 16.4 | 15.4 | 13.2 | 12.1 | 11.4 |
| 9 | 20.1 | 16.6 | 15.5 | 13.7 | 12.4 | 11.5 |

Parameters of the calibration curve:
slope: 3.68116955
section of the axis: 13.692153
correlation coeff.: .994836289

TABLE 7

| No of the animal | Primycin concentration | | | | | |
|---|---|---|---|---|---|---|
| | Day 0 | Day 1 | Day 2 | Day 3 | Day 4 | Day 5 |
| 1. | 0 | 0 | 0 | 0 | 0 | 0 |
| 2. | 0 | 0 | 0 | 0 | 0 | 0 |
| 3. | 0 | 0 | 0 | 0 | 0 | 0 |
| 4. | 0 | 0 | 0 | 0 | 0 | 0 |
| 5. | 0 | 0 | 0 | 0 | 0 | 0 |
| 6. | 0 | 0 | 0 | 0 | 0 | 0 |
| 7. | 0 | 0 | 0 | 0 | 0 | 0 |
| 8. | 0 | 0 | 0 | 0 | 0 | 0 |
| 9. | 0 | 0 | 0 | 0 | 0 | 0 |
| 10. | 0 | 0 | 0 | 0 | 0 | 0 |
| 11. | 0 | 0 | 0 | 0 | 0 | 0 |
| 12. | 0 | 0 | 0 | 0 | 0 | 0 |
| 13. | 0 | 0 | 0 | 0 | 0 | 0 |
| 14. | 0 | 0 | 0 | 0 | 0 | 0 |
| 15. | 0 | 0 | 0 | 0 | 0 | 0 |
| 16. | 0 | 0 | 0 | 0 | 0 | 0 |
| 17. | 0 | 0 | 0 | 0 | 0 | 0 |
| 18. | 0 | 0 | 0 | 0 | 0 | 0 |
| 19. | 0 | 0 | 0 | 0 | 0 | 0 |
| 20. | 0 | 0 | 0 | 0 | 0 | 0 |
| 21. | 0 | 0 | 0 | 0 | 0 | 0 |
| 22. | 0 | 0 | 0 | 0 | 0 | 0 |
| 23. | 0 | 0 | 0 | 0 | 0 | 0 |
| 24. | 0 | 0 | 0 | 0 | 0 | 0 |
| 25. | 0 | 0 | 0 | 0 | 0 | 0 |
| 26. | 0 | 0 | 0 | 0 | 0 | 0 |
| 27. | 0 | 0 | 0 | 0 | 0 | 0 |
| 28. | 0 | 0 | 0 | 0 | 0 | 0 |
| 29. | 0 | 0 | 0 | 0 | 0 | 0 |
| 30. | 0 | 0 | 0 | 0 | 0 | 0 |
| 31. | 0 | 0 | 0 | 0 | 0 | 0 |
| 32. | 0 | 0 | 0 | 0 | 0 | 0 |
| 33. | 0 | 0 | 0 | 0 | 0 | 0 |
| 34. | 0 | 0 | 0 | 0 | 0 | 0 |
| 35. | 0 | 0 | 0 | 0 | 0 | 0 |
| 36. | 0 | 0 | 0 | 0 | 0 | 0 |
| 37. | 0 | 0 | 0 | 0 | 0 | 0 |
| 38. | 0 | 0 | 0 | 0 | 0 | 0 |
| 39. | 0 | 0 | 0 | 0 | 0 | 0 |
| 40. | 0 | 0 | 0 | 0 | 0 | 0 |

0 = no primycin concentration was detected in the serum

Post Mortem Examination of the Skin Irritation of Rabbits Treated with Primycin for 5 Days' Dermal Application Forty New Zealand rabbits, 20 males and 20 females, were submitted to autopsy. Developmental and physical state of the animals corresponded to their age and species. Visible mucous membranes and conjunctivae were intact and porcelain white. In the upper third of the back of the animals in the line of the spinal cord there was a depilated area of $3 \times 5$ cm where the preparation had been applied. This skin area was examined.

Grouping 1-3—depilated male, primycin sample 1
4-6—depilated female, primycin sample 1
7-9—depilated male, primycin sample 2
10-12—depilated female, primycin sample 2
13-15—depilated male, primycin sample 3
16-18—depilated female, primycin sample 3
19-21—depilated, scarified, male, primycin sample 1
22-24—depilated, scarified, female, primycin sample 1
25-27—depilated, scarified, male, primycin sample 2
28-30—depilated, scarified, female, primycin sample 2
31-33—depilated, scarified, male, primycin sample 3
34-36—depilated, scarified, female, primycin sample 3
37—depilated male, control sample 4
38—depilated female, control sample 4
39—depilated, scarified male, control sample 4
40—depilated, scarified female, control sample 4.

Description of the Observed Alterations

Rabbit 5: a small pepper-sized crust extending to the stratum corneum.
Rabbit 8: a lentil-sized crust extending to the cutis.
Rabbit 12: a small pepper-sized crust extending to the stratum corneum.
Rabbits 13, 14, 15 and 16: lentil-sized squamification extending to the stratum corneum.
Rabbit 28: a small pepper-sized crust extending to the stratum corneum.
Rabbit 31: a small pepper-sized crust extending to the stratum corneum.
Rabbit 33: a crust of $3 \times 1$ cm area extending to the stratum germinativum.
No alterations were detected in the other animals their skin was perfectly intact.

Skin alterations found at autopsy were slight and they did not extend to deep layers. The majority of changes was detected in the animals treated with sample 3. This is probably due to the fact that sample 3 had desiccated the skin which became cracked and subject to crustation.

SOLUBILITY OF PRIMYCIN AND OTHER COMPOUNDS IN N-METHYL-PYRROLIDONE

We have examined the quantity in ml of N-methylpyrrolidone which is necessary to dissolve 0.1 gram of each respective compound. The results of the examination are in the following Table 8:

| | Required Amount of N-methyl pyrrolidone in milliliters necessary to dissolve 0.1 g | |
|---|---|---|
| Compound | (A) Room Temperature | (B) Under Heating |
| Doxycycline | 10.0 | 2.0 |
| Hydrocortisone-Acetate | 1.0 | 0.2 |
| Nystatin | 5.0 | 2.0 |
| Albendazole | 1.5 | 1.0 |
| Streptomycin Sulfate | 20.0 | does not dissolve |
| Nalidixic Acid | does not dissolve | 6.0 (significant heating needed, precipitates after cooling). |
| atronidazole | 3.0 | 1.0 |
| Oxolinic Acid | does not dissolve | 8.0 (significant heating needed, precipitates after cooling). |
| Primycin | does not dissolve | 0.5 |

Thus primycin itself is not easily dissolved in N-methyl-pyrrolidone and there is no simple rule concerning the solubility of other compounds in N-methyl-pyrrolidone, either at room temperature or elevated temperature.

Thus there would be no basis to predict that a stable primycin gel prepared by dissolving primycin in N-methyl-pyrrolidone at 100° C., and thereafter cooling the solution to room temperature would result in a stable primycin gel.

What we claim is:

1. Primycin-containing colloidal basic gel comprising 5 to 30% of primycin and 95 to 70% by weight of N-methyl-pyrrolidone-2 prepared by dissolving the primycin in the N-methyl-pyrrolidone-2 at a temperature of 70° to 150° C. to form a solution followed by cooling the solution to room temperature.

2. The primycin-containing colloidal basic gel defined in claim 1 comprising 10 to 20% of primycin and 90 to 80% of N-methyl-pyrrolidone-2.

3. A colloidal basic gel which comprises:
   (a) a primycin-containing gel prepared by dissolving 5 to 12% primycin in 20 to 48% N-methyl-pyrrolidone-2 at a temperature of 70° to 150° C. to form a solution followed by cooling the solution to room temperature;
   (b) 10 to 60% of a second antibiotic agent selected from the group consisting of nystatin, doxycycline and gentamycin; and
   (c) 15 to 30% water.

4. The colloidal basic gel defined in claim 3 which comprises 10% primycin, 40% N-methyl-pyrrolidone-2, 20% of the second antibiotic agent defined in claim 3, and 30% water.

5. The colloidal basic gel defined in claim 3 wherein gentamycin or doxycycline is the second antibiotic agent.

6. An antibacterial composition for the treatment of acne vulgaris or mastitis which comprises a therapeutically effective amount of the primycin-containing colloidal basic gel defined in claim 1 together with a pharmaceutically acceptable inert carrier.

7. An antibacterial composition for the treatment of acne vulgaris or mastitis which comprises a therapeutically effective amount of the primycin-containing colloidal basic gel defined in claim 3 together with a pharmaceutically acceptable inert carrier.

8. An antibacterial method of treatment which comprises the step of applying to the skin of an animal subject with a bacterial infection of the skin, a therapeutically effective amount of the primycin gel defined in claim 1.

9. The antibacterial method of treatment defined in claim 8 wherein the bacterial infection is mastitis or acne vulgaris.

10. An antibacterial method of treatment which comprises the step of applying to the skin of an animal subject with a bacterial infection of the skin, a therapeutically effective amount of the primycin gel defined in claim 3.

11. The antibacterial method of treatment defined in claim 10 wherein the bacterial infection is mastitis or acne vulgaris.

* * * * *